United States Patent
Airenne et al.

(10) Patent No.: US 7,393,677 B2
(45) Date of Patent: Jul. 1, 2008

(54) AVIDIN-PSEUDOTYPED VIRAL VECTORS AND THEIR USE

(75) Inventors: Kari Juhani Airenne, Kuopio (FI); Anssi Mahonen, Kuopio (FI); Seppo Yla-Herttuala, Kuopio (FI)

(73) Assignee: Ark Therapeutics, Ltd. (GB)

( * ) Notice: Subject to any disclaimer, the term of this patent is extended or adjusted under 35 U.S.C. 154(b) by 0 days.

(21) Appl. No.: 11/481,674

(22) Filed: Jul. 6, 2006

(65) Prior Publication Data

US 2006/0246091 A1  Nov. 2, 2006

Related U.S. Application Data

(63) Continuation of application No. 10/471,488, filed as application No. PCT/GB02/01120 on Mar. 12, 2002, now abandoned.

(30) Foreign Application Priority Data

Mar. 12, 2001 (GB) ............................. 0106064.9
Mar. 12, 2001 (GB) ............................. 0106066.4

(51) Int. Cl.
*C12N 7/01* (2006.01)
*C12N 15/866* (2006.01)
*C12N 15/62* (2006.01)

(52) U.S. Cl. ............... 435/235.1; 435/320.1; 435/455; 435/456; 424/199.1; 424/93.2; 536/23.4

(58) Field of Classification Search ............. 435/320.1, 435/69.3, 456, 69.1, 173.3, 5; 424/93.2, 424/93.21

See application file for complete search history.

(56) References Cited

U.S. PATENT DOCUMENTS

| | | | | |
|---|---|---|---|---|
| 5,244,805 A * | 9/1993 | Miller | ............. | 435/320.1 |
| 5,731,182 A | 3/1998 | Boyce | | |
| 5,789,245 A * | 8/1998 | Dubensky et al. | ......... | 435/320.1 |
| 6,015,694 A * | 1/2000 | Dubensky et al. | .......... | 435/69.3 |
| 7,018,628 B1 * | 3/2006 | Sarkis et al. | ............. | 424/93.2 |
| 2001/0049144 A1 * | 12/2001 | Rivera et al. | ............. | 435/456 |
| 2003/0054010 A1 | 3/2003 | Sebbel et al. | | |
| 2004/0028653 A1 | 2/2004 | Seed et al. | | |

FOREIGN PATENT DOCUMENTS

| | | |
|---|---|---|
| WO | WO 97 05266 A1 | 2/1997 |
| WO | WO 99 09193 A1 | 2/1999 |
| WO | WO 99/19500 | 4/1999 |
| WO | WO 00 77233 A2 | 12/2000 |

OTHER PUBLICATIONS

Horlick et al., "Rapid Generation of Stable Cell Lines Expressing Corticotropin-Releasing Hormone Receptor for Drug Discovery," Protein Expression and Purification, 9, pp. 301-308 (1997).*

Shoji et al., "Efficient gene transfer into various mammalian cells, including non-hepatic cells, by baculovirus vectors," Journal of General Virology, 78, pp. 2657-2664 (1997).*

Tomiyasu et al., "Gene Transfer in vitro and in vivo with Epstein-Barr Virus-Based Episomal Vector Results in Markedly High Transient Expression in Rodent Cells," Biochemical and Piophysical Research Communications, 253, pp. 733-738 (1998).*

Langle-Rouault et al., "Up to 100-Fold Increase of Apparent Gene Expression in the Presence of Esptein-Barr virus oriP and EBNA1: Implications of the Nuclear Import of Plasmids," Journal of Virology, vol. 72, No. 7, pp. 6181-6185 (1998).*

Zavada, "The Pseudotypic Paradox," J Gen Virol, 63, 15-24 (1982).*

Badie et al., "Combined radiation and p53 gene therapy of malignant glioma cells," Cancer Gene Therapy, vol. 6, No. 2, pp. 155-162 (1999).*

Airenne et al., "Baculovirus-mediated periadventitial gene transfer to rabbit carotid artery," Gene Therapy, 7, pp. 1499-1504 (2000).*

Smith et al., "Redirected Infection of directly biotinylated recombinant adenovirus vectors through cell surface receptors and antigens," PNAS, vol. 96, pp. 8855-8860 (1999).*

Kreda et al., "G-protein-coupled receptors as targets for gene transfer vectors using natural small-molecule ligands," Nature Biotechnology, vol. 18, pp. 635-640 (2000).*

Vinogradov et al., "Polyion Complex Micelles with Protein-Modified Corona for Receptor-Mediated Delivery of Oligonucleotides into cells," Bioconjugate Chem, 10, pp. 851-860 (1999).*

Lu et al., "Semliki Forst Virus Budding: Assay, Mechanisms, and Cholesterol Requirement," Journal of Virology, vol. 74, No. 17, pp. 7708-7719 (2000).*

Sanders, D.A. "No False Start for Novel Pseudotyped Vectors" *Current Opinion in Biotechnology*, 2002, pp. 437-442,vol. 13.

Raty, J.R. et al. "Enhanced Gene Delivery by Avidin-Displaying Baculovirus" *Molecular Therapy*, Feb. 2004, pp. 282-291, vol. 9, No. 2.

Williams, D.A. et al. "Gene Therapy-New Challenges Ahead" *Science*, Oct. 2003, pp. 400-401, vol. 302.

Phillips, A.J. The Challenge of Gene Therapy and DNA Delivery *Journal of Pharmacy and Pharmacology*, 2001, pp. 1169-1174, vol. 53.

Chapple, S.D.J et al. "Non-Polar Distribution of Green Fluorescent Protein on the Surface of *Autographa californica* Nucleopolyhedrovirus using a Heterologous Membrane Anchor" *Journal of Biotechnology*, 2002, pp. 269-275, vol. 95.

Borg, J. et al. "Amino-Terminal Anchored Surface Display in Insect Cells and Budded Baculovirus using the Amino-Terminal End of Neuraminidase" *Journal of Biotechnology*, 2004, pp. 21-30, vol. 114.

(Continued)

*Primary Examiner*—Mary E Mosher
(74) *Attorney, Agent, or Firm*—Saliwanchik, Lloyd & Salinwanchik

(57) ABSTRACT

The present invention pertains to an avidin-pseudotyped virus, and especially baculovirus, useful for delivery of foreign genes etc. The present invention also pertains to vectors comprising respective cassettes for pseudotyping, mammalian gene expression and insect gene expression in baculovirus.

7 Claims, 2 Drawing Sheets

OTHER PUBLICATIONS

Lung, O.Y. et al. "Ac23, an Envelope Fusion Protein Homolog in the *Baculovirus californica* Multicapsid Nucleopolyhedrovirus, Is a Viral Pathogenicity Factor" *Journal of Virology*, Jan. 2003, pp. 328-339, vol. 77, No. 1.

Loisel, T.P. et al. "Recovery of Homogeneous and Functional Beta-2-Adrenergic Receptors from Extracellular Baculovirs Particles" *Nature Biotechnology*, Nov. 1997, pp. 1300-1304, vol. 15, No. 12, Abstract only.

Urano, Y. et al. "A Novel Method for Viral Display of ER Membrane Proteins on Budded Baculovirus" *Biochemical and Biophysical Research Communications*, 2003, pp. 191-196, vol. 308.

Kazuyuki, M. et al. "A Combinatorial G Protein-Coupled Receptor Reconstitution System on Budded Baculovirus" *Journal of Biological Chemistry*, Jul. 2003, pp. 24552-24562, vol. 278, No. 27.

Ikuo, H. et al. "Selective Reconstitution and Recovery of Functional γ-Secretase Complex on Budded Baculovirus Particles" *Journal of Biological Chemistry*, Sep. 2004, pp. 38040-38046, vol. 279, No. 36.

* cited by examiner

AVIDIN-PSEUDOTYPED VIRAL VECTORS AND THEIR USE

CROSS-REFERENCE TO RELATED APPLICATION

This application is a continuation of U.S. application Ser. No. 10/471,488, filed Mar. 15, 2004, now abandoned, which is the U.S. national stage application of International patent application No. PCT/GB02/01120, filed Mar. 12, 2002, the disclosure of each of which is hereby incorporated by reference in its entirety including any tables, figures, or drawings.

FIELD OF THE INVENTION

This invention relates to viral vectors and their use.

BACKGROUND OF THE INVENTION

Chicken egg-white avidin and bacterial streptavidin (from *Streptomyces avidinhi*) are tetrameric proteins which bind biotin with similar affinity constants (Ka $\sim 10^{15}$ $M^{-1}$), the strongest protein-ligand interaction known in nature. This affinity, together with the facile incorporation of the biotin moiety into various binders and probes, has served to promote the widely used avidin-biotin technology.

Despite extensive knowledge about the properties of avidin, little is known about its biological function. Since the growth of a number of microorganisms is inhibited by avidin, and its occurrence after tissue damage has been clearly demonstrated, it most likely has a role as a host defence factor.

Enhanced cellular uptake of avidin-coated vectors has been reported (Pardridge and Boado, *FEBS Lett.* 288: 30-32, 1991; Vinogradov *Bioconjug. Chem.* 10: 851-860, 1999). Also, polylysine (net positive charge at physiological pH) has been used to pseudotype adenovirus and shown to augment gene transfer to a variety of CAR-deficient cell types, including macrophages, smooth muscle cells, fibroblasts, endothelial cells, T cells, glioma cells, acute myeloid leukemic cells, myeloma cells and skeletal muscle cells (Wickham et al., *J. Virol.* 71: 8221-8229, 1997; Hidaka et al., *J. Clin. Invest.* 103: 579-587, 1999; Yoshida et al., *Hum. Gene Ther.* 9: 2503-2515, 1998; Gonzalez et al., *Hum. Gene Ther.* 10: 2907-2717, 1999; Gonzalez et al., *Gene Ther.* 6: 314-320, 1999). Furthermore, it has been shown that biotin attached to cell surface membrane proteins enables efficient entry of avidin bioconjugates into nucleated cells.

Avidin has been used for drug targeting; in vivo studies have shown that avidin preferentially accumulates into certain tissues, including tumour tissue (Yao et al., *J. Nat. Cancer Inst.* 90: 25-29, 1998; Rosebrough and Hartley, *J. Med.* 37: 1380-1384, 1996).

Gene therapy is a highly potent and rapidly developing field of research aimed at treat or prevent disease by gene transfer. Currently, the most efficient vectors are viral. However, the low efficiency of gene transfer still limits successful gene therapy and there is a need for more facile and efficient gene transfer vectors. The ideal vector should also be capable of cell-specific gene delivery in order to provide the therapeutic effect where needed, in contrast to uncontrolled gene transfer to normal tissues and organs.

Although transient expression may be desired and/or sufficient in gene therapy of cancer or cardiovascular diseases, more prolonged transgene expression is needed for treatment of inherited metabolic disorders such as severe combined immunodeficiency (SCID).

The origin of replication (orip) of the Epstein-Barr virus (EBV) supports stable replication of plasmids, and the cloned cDNAs they contain, in proliferating cells from many species. In cells expressing Epstein-Barr nuclear antigen I (EBNAI), plasmids containing oriP replicate during S phase and segregate to daughter cells efficiently. The number of plasmids per cell is stable.

Baculoviruses have long been used as biopesticides (Cory and Bishop, 1997) and as tools for efficient recombinant protein production in insect cells. They are generally regarded as safe due to the naturally high species-specificity and because they are not known to propagate in any non-invertebrate host. They are incapable of replication in mammalian cells, and have a large capacity for the insertion of foreign sequences into the genome.

BRIEF SUMMARY OF THE INVENTION

According to one aspect of the present invention, novel vectors are avidin-pseudotyped viral vectors. They can offer an elegant solution to the problems of gene therapy, for several reasons. Firstly, avidin as such can widen the tissue tropism of a desired virus vector because of its high pI (~10.5=high net positive charge at physiological pH).

Secondly, avidin may allow tissue targeting of pseudotyped viruses in vivo. This tissue tropism can be affected by modifying physicochemical properties of avidin (i.e. deglycosylated and/or p1-variant of avidin). For example, a series of avidin mutants is known (Marttila et al, *FEBS Lett.* 441: 313-317, 1998; Marttila et al., *FEBS Lett.* 467: 31-36, 2000) which may prove to be valuable in this sense.

Thirdly, in addition to the possible benefits of the intrinsic properties of avidin, the irreversible and tight biotin-binding ability of avidin (as well as related proteins, e.g. streptavidin and like proteins such as streptavidin V1&2; avidin-related genes, avrs; or sea urchin fibrobellin) may further increase the gene delivery efficiency, enlarge or restrict the tissue tropism, and improve stability of avidin-pseudotyped viruses. This may be achieved by mixing avidin-pseudotyped viruses with biotinylated molecules like targeting ligands, e.g. proteins, peptides or oligosaccharides, endosome-disruptive peptides/molecules, nuclear localizing signals and biotinylated-PEG molecules; see, for example, Vinogradov et al., supra. An additional advantage of this strategy is that it enables coating of viruses with different combinations of these molecules. There is support for this in the redirected infection of directly biotinylated adenovirus through an avidin bridge (Smith et al., *PNAS USA,* 96: 8855-8860, 1999).

Lastly, but not least, avidin-biotin technology offers the possibility of using avidin-pseudotyped vectors, to study attachment, internalization, endosomal fusion, lysosomal routing, and nuclear accumulation of these viruses. Avidin-pseudotyped viruses thus offer versatile gene delivery tools for in vivo and in vitro purposes, which combine the advantages of avidin-biotin technology to gene transfer purposes.

For the purposes of this specification, "avidin" is used in its broadest sense, i.e. as a biotin-binding molecule. Similarly, "biotin" is used to indicate a molecule that binds avidin. The term "virus" includes infectious particles.

According to a second aspect of the present invention, and in order to prolong the naturally transient baculovirus-mediated transgene expression in vitro and in vivo, EBV oriP and EBNAI or functional equivalents thereof are integrated as part of a versatile baculovirus vector (VBV) cassette. These elements may be provided in the form of a plasmid.

BRIEF DESCRIPTION OF THE DRAWINGS

The invention will now be described by way of example only with reference to the accompanying drawings, in which.

DETAILED DISCLOSURE OF THE INVENTION

Figure 1:
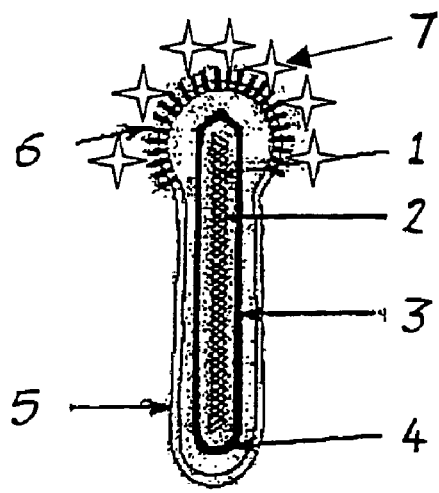
FIG. 1 shows a schematic presentation of an avidin-pseudotyped embodying the present invention (hereinafter described as BAAVI).

The embodiment shown in FIG. 1 comprises DNA 1 including basic DNA-binding protein (p6.9) 2, major capsid proteins (vp39, p80, p24) 3, and a capsid end structure (ORF 1629) 4. The baculovirus also comprises a virion envelope 5, typically having a membrane lipid composition comprising 5.9% LPC, 13.2% SPH, 10.7% PC, 12.3% PI, 50.2% PS and 7.6% PE.

Figure 2:
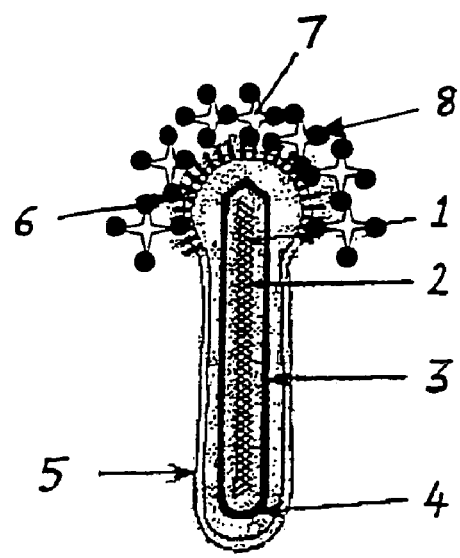
FIG. 2 shows a schematic presentation similar to that of FIG. 1, showing BAAVI coated with biotinylated molecules.

The embodiment shown in FIG. 1 further comprises gp64 envelope fusion protein (gp64 EFP) 6 and avidin molecules 7. FIG. 2 additionally shows biotinylated molecules 8 bound to avidin.

In practice, BAAVI is prepared essentially as described by Boublik et al., *Biotechnology* (NY) 13: 1079-1084, 1995. Due to possible folding problems as a consequence of fusing together tetrameric avidin and trimeric major envelope glycoprotein of AcMNPV (gp64), six different versions of BAAVI were constructed, i.e. baculovirus bearing in its envelope natural avidin/gp64, reavidin/gp64 (Airenne et al., *Protein Expr. Purif.* 9: 100-108, 1997), dimeric-avidin/gp64 (Laitinen et al., *FEBS Lett.* 461: 52-58, 1999), monomeric-avidin$^{-b}$/gp64 (avidin monomeric in the absence of biotin, two forms; Marttila et al., supra) and monomeric-avidin/gp64.

Avidin-encoding sequences are amplified by polymerase chain reaction (PCR) and cloned into Pst1-site of modified pFASTBAC1-vector (pfbac1pg64) in frame between the upstream AcMNPV gp64 signal sequence and downstream gp64 mature domain (this expression cassette is cloned from pBACsurf-1 plasmid, Novagen, into PFASTBAC1). The pfbac1gp64-vector is compatible with Bac-TO-Bac™ baculovirus expression system (Gibco BRL) which allows rapid and easy preparation of recombinant by site-specific transposition in *Escherichia coli*. Gradient-purified recombinant baculoviruses (BAAVI5) may be studied by blotting techniques and electron microscopy for avidin-pseudotyping.

Coating of BAAVI (FIG. 2) may be performed by mixing it with desired biotinylated molecule(s). Suitable cell lines (e.g. RAASMC, Rabbit and human fibroblasts, ECV-304 etc.) are transduced or infected (sf9 or High five) with BAAVI5 or coated-BAAVI5. Transfection efficiency may be compared to native viruses using nuclear-targeted β-galactosidase, green- and red fluorescent proteins as transgene and standard cell culture and microscopical methods. In vivo effects of avidin-pseudotyping per se and effects of desired molecule(s) coating to BAAVIs cell (tissue) trophism may be studied by a local gene delivery method (collar or direct injection), using rabbits and rats and standard microscopical and histological methods. In order to study the baculovirus entry into cells, biotinylated molecules such as FITC-biotin can be used to coat BAAVI and followed during different steps of infection (insect cells) or transduction (in mammalian cells) by standard cell culture and microscopical methods.

Figure 3:
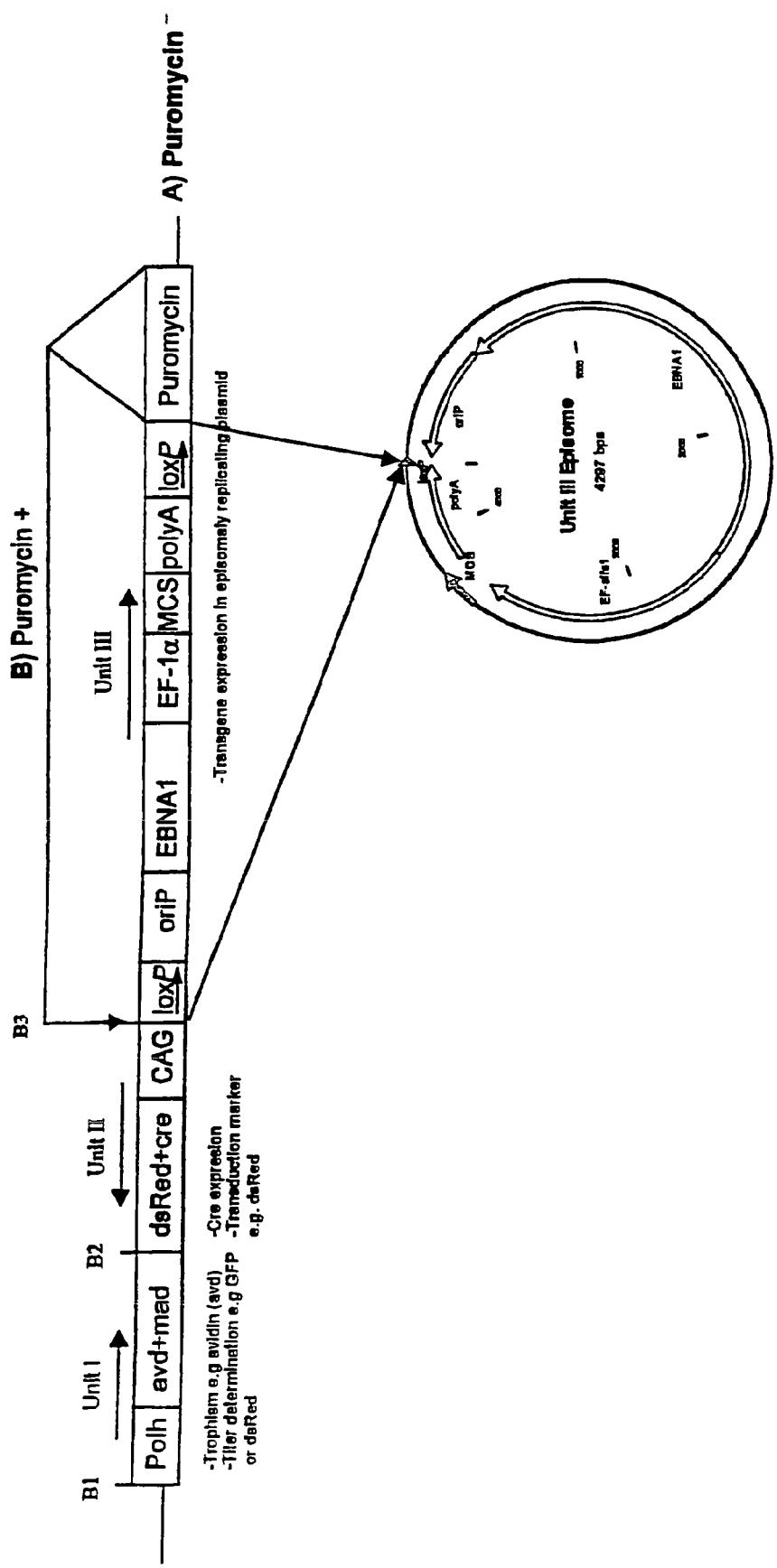
FIG. 3 shows a schematic representation of a versatile baculovirus vector embodying the invention.

FIG. 3 shows a fragment which consists of Units I-III cloned in pFasbac1 donor baculovirus expression system (Gibco BRL) and allows rapid and easy preparation of re-baculoviruses. Polh; polyhedrin promoter. Avd; avidin. Mad; membrane anchoe domain of gp64. DsRed; red fluorescent protein. Cre; cre recombinase. CAG; chicken β-actin promoter. LoxP; cre site-specific recombination site. OriP; EBV origin of replication. EBNAI; EBV nuclear antigen 1. EF-1α; elongation factor-1 alpha promoter. MCS; multiple cloning site. PolyA; polyadenylation site. Puromycin; puromycin resistance gene. B1-3; blunt-end yielding restriction enzyme 1-3.→; direction of the unit promoter or loxP.

In a preferred embodiment of a versatile baculovirus vector according to the invention, and in order to excise an EBV-episome from a target recombinant baculovirus genome in the target cell (tissue), these episomal replication-allowing sequences, together with therapeutic transgene cassette, are put under cre-meditated site-specific recombination (Sauer, *Methods* 14: 381-392, 1998) into Unit III (transgene unit) of VBV. If desired, the transgene unit can be constructed without the cre-controlled episomal replication elements and replaced only with desirable (inducible and/or tissue-specific) promoter and transgene.

In addition to a transgene unit (FIG. 3, unit III), the VBV cassette may also contain two additional units. Unit 1 (FIG. 3, unit 1) operates under a polyhedrin promoter and can be used to modify the baculovirus phenotype (e.g used for pseudotyping the virus, see BAAVI), since the polyhedrin promoter is active only in insect cells. Optionally, this unit can also be used e.g. to integrate marker gene (e.g. GFP or dsRed) into the virus, in order to help titering of the viruses in the insect cells.

Unit II (FIG. 3, unit II) allows expression of, say, a marker gene (GFP, red fluorescent protein, nuclear-targeted β-galactosidase, etc.), e.g under GAG-promoter (Niwa et al., *Gene* 108: 193-199, 1991; Miyazaki et al., *Gene* 79: 269-277, 1989) as a sign of successful transduction of target cell or tissue. Unit II gives thus also an indirect evidence of successful delivery of therapeutic transgene. The advantages of this strategy as well as GFP in this sense (Yang et al., 2000).

The VBV cassette is flexible. If desired, each unit in the VBV can be cut with a blunt-end-yielding restriction enzyme (FIG. 3 81-3) and replaced by an improved unit. Moreover, units not needed can be cleaved off.

In a preferred embodiment, in order to construct a VBV cassette, suitable DNA sequences are cloned into pFastbac1 donor vector backbone (Gibco BRL). The VBV cassette can be easily cloned from this vector into virtually any baculovirus donor plasmid. pFastbac1 was chosen as first choice backbone-plasmid since it is compatible with Bac-TO-Bac™ expression system (Gibco BRL) which allows rapid and easy preparation of re-baculoviruses by site-specific transposition in *Escherichia coli*. Unit I sequence is cloned e.g. from BAAVI (allows avidin-pseudotyping). Unit II is constructed e.g. from pDsRed1-N1 (Clontech, dsRED) and pBS185 (Ore expression vector, Gibco BRL) by fusing cre sequence to dsRED under GAG promoter (taken from pCAGGS). Unit III is constructed from loxP modified pEAKI 2 vector (Edge Biosystems). Nuclear-targeted β-galactosidase gene is cloned into multiple cloning site (MCS; the transgene cloning site) of Unit III. In alternative versions of the VBV cassette, a therapeutic gene (e.g. VEGF, PR39) will replace it.

The functionality and gene delivery efficiency of prepared viruses may be studied by standard cell culture and microscopical methods. A control virus lacking VBV-cassette is used as a control, to study the duration of transgene expression. Rabbits and rats may be used for in vivo characterisation of the VBV along with standard histological methods. PCR may be used for characterisation of efficiency of cre-lox based episome formation in the cells. Ore expression may be studied by immunoblotting using cre-specific antibody (Novagen).

More generally, a vector of the invention may be utilised to deliver a foreign gene or gene product. This may have any desired, known function. It may be, for example, a therapeutic or diagnostic protein or peptide, an antisense oligonucleotide, a ribozyme or catalytic DNA or RNA. Further, although reference has been made above to specific commercial vectors, it would be appreciated that any suitable baculovirus plasmid or baculovirus system may be used.

We claim:

1. A baculovirus which has been modified wherein envelope proteins of said baculovirus include avidin.

2. The baculovirus according to claim 1, coated with a biotinylated molecule.

3. The baculovirus according to claim 1, which comprises a foreign gene which has, or is capable of expressing a peptide having diagnostic or therapeutic utility.

4. A method for delivering a foreign gene into the genome of a target cell, comprising:
   contacting said cell with a baculovirus of claim 1, wherein said baculovirus comprises said foreign gene.

5. The method according to claim 4, wherein said foreign gene encodes a gene product selected from the group consisting of a therapeutic protein or peptide, a diagnostic protein or peptide, an antisense oligonucleotide, a catalytic DNA, and a ribozyme or catalytic RNA.

6. The baculovirus according to claim 1, wherein said baculovirus can bind biotin.

7. The baculovirus according to claim 1, wherein said baculovirus comprises a fusion protein comprising baculovirus envelope protein and avidin.

* * * * *